United States Patent
Yao et al.

(10) Patent No.: US 11,597,689 B2
(45) Date of Patent: Mar. 7, 2023

(54) DUAL STAGE LIGHT ALKANE CONVERSION TO FUELS

(71) Applicant: PHILLIPS 66 COMPANY, Houston, TX (US)

(72) Inventors: Jianhua Yao, Bartlesville, OK (US); Hong Xie, Bartlesville, OK (US); Jonathan Marda, Bartlesville, OK (US); Dhananjay Ghonasgi, Bartlesville, OK (US); Sourabh Pansare, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 282 days.

(21) Appl. No.: 17/076,299

(22) Filed: Oct. 21, 2020

(65) Prior Publication Data

US 2021/0122687 A1 Apr. 29, 2021

Related U.S. Application Data

(60) Provisional application No. 62/925,016, filed on Oct. 23, 2019.

(51) Int. Cl.
| | |
|---|---|
| *C07C 2/42* | (2006.01) |
| *C07C 7/09* | (2006.01) |
| *C07C 2/12* | (2006.01) |
| *B01J 8/02* | (2006.01) |
| *B01J 8/00* | (2006.01) |

(52) U.S. Cl.
CPC ............... *C07C 2/42* (2013.01); *B01J 8/001* (2013.01); *B01J 8/02* (2013.01); *C07C 2/12* (2013.01); *C07C 7/09* (2013.01); *B01J 2208/00017* (2013.01); *B01J 2208/00539* (2013.01); *B01J 2208/027* (2013.01); *C07C 2529/40* (2013.01)

(58) Field of Classification Search
CPC .... C07C 2/42; C07C 2/12; C07C 7/09; C07C 2529/40; B01J 8/001; B01J 8/02; B01J 2208/00017; B01J 2208/00539; B01J 2208/027
See application file for complete search history.

(56) References Cited

U.S. PATENT DOCUMENTS 4,487,985 A * 12/1984 Tabak ................ C07C 2/12
585/533
4,560,536 A * 12/1985 Tabak ................ C07C 2/12
208/135

(Continued)

*Primary Examiner* — Ali Z Fadhel
(74) *Attorney, Agent, or Firm* — Phillips 66 Company

(57) ABSTRACT

A process and system for the conversion of a feedstock comprising C3-C5 light alkanes to a C5+ hydrocarbon product, for example, a BTX-rich hydrocarbon product, by performing the alkane activation (first-stage) and the oligomerization/aromatization (second-stage) in separate stages, which allows each conversion process to occur at optimal reaction conditions thus increasing the overall hydrocarbon product yield. The alkane activation or first-stage is operated at a higher temperature than the second-stage since light alkanes are much less reactive than light olefins. Since aromatization of olefins is more efficient at higher pressure, the second-stage is maintained at a higher pressure than the first-stage. Further, fixed-bed catalysts are used in each of the first-stage and the second-stage.

20 Claims, 1 Drawing Sheet

(56) References Cited

U.S. PATENT DOCUMENTS

| | | | |
|---|---|---|---|
| 4,788,364 A | 11/1988 | Harandi | |
| 4,808,295 A * | 2/1989 | Nemet-Mavrodin | B01J 29/405 585/419 |
| 4,919,896 A * | 4/1990 | Harandi | C07C 2/00 422/142 |
| 5,292,976 A * | 3/1994 | Dessau | C10G 59/02 208/62 |
| 5,523,502 A * | 6/1996 | Rubin | C10G 69/06 585/314 |
| 2002/0099248 A1* | 7/2002 | Ziaka-Vasileiadou | C07D 301/19 585/324 |
| 2008/0161620 A1* | 7/2008 | Bozzano | C07C 6/126 422/600 |
| 2010/0041930 A1* | 2/2010 | Gartside | C07C 6/04 585/314 |
| 2011/0087000 A1* | 4/2011 | Peters | C07C 5/03 585/240 |
| 2011/0152594 A1* | 6/2011 | Brown | C10G 3/49 585/408 |
| 2013/0131414 A1* | 5/2013 | Iyer | C07C 2/76 48/197 FM |
| 2015/0126628 A1* | 5/2015 | Patience | C01B 3/38 518/703 |
| 2019/0367432 A1* | 12/2019 | Al-Majnouni | C10G 51/026 |
| 2020/0179917 A1* | 6/2020 | Liu | B01J 29/70 |
| 2021/0355050 A1* | 11/2021 | Fletcher | C10G 11/05 |
| 2021/0395178 A1* | 12/2021 | Barias | C07C 2/08 |

* cited by examiner

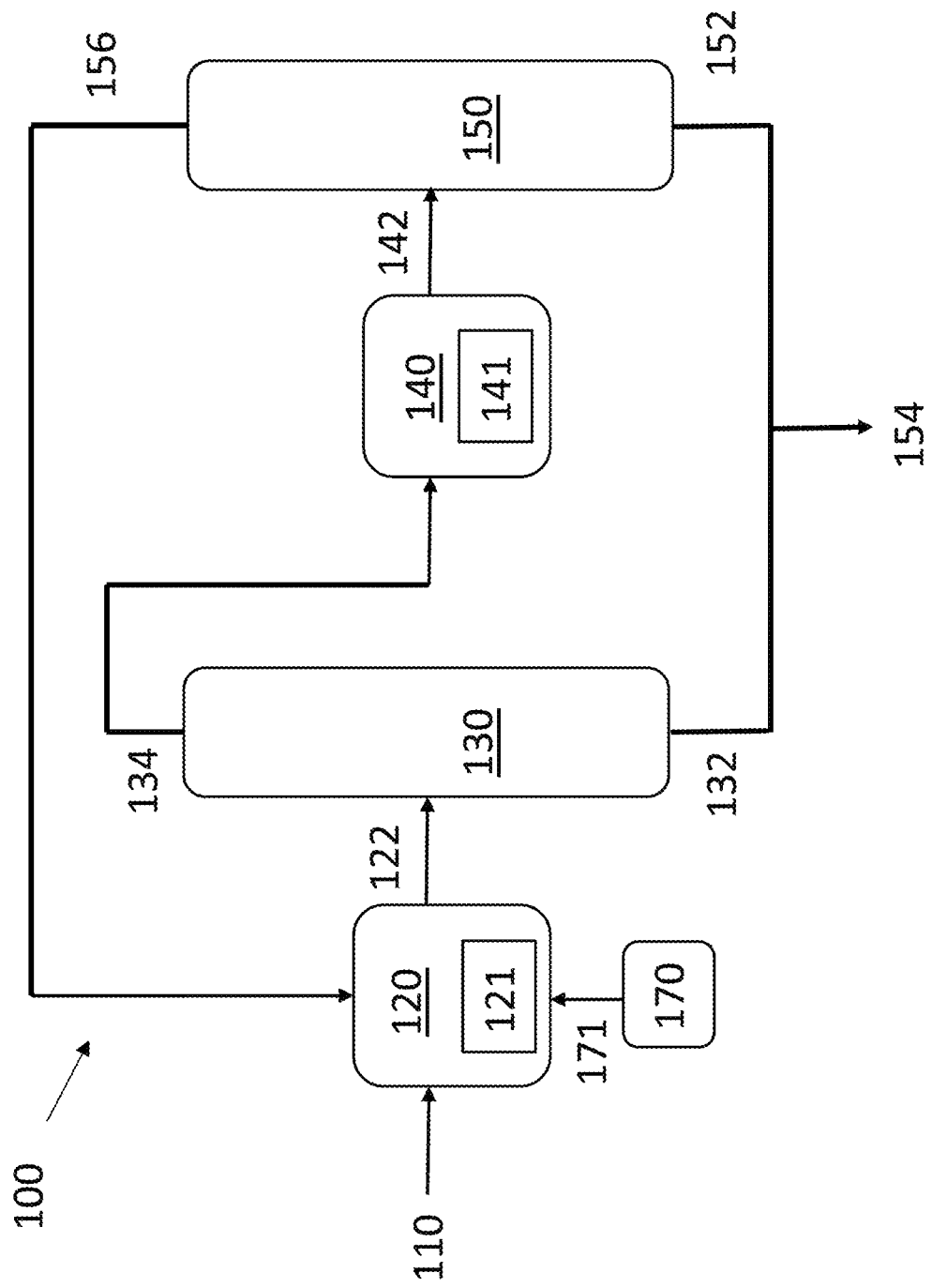

DUAL STAGE LIGHT ALKANE CONVERSION TO FUELS

CROSS-REFERENCE TO RELATED APPLICATIONS

This application is a non-provisional application which claims the benefit of and priority to U.S. Provisional Application Ser. No. 62/925,016 filed Oct. 23, 2019, titled "Dual Light Alkane Conversion to Fuels," which is hereby incorporated by reference in its entirety.

STATEMENT REGARDING FEDERALLY SPONSORED RESEARCH OR DEVELOPMENT

None.

FIELD OF THE INVENTION

The present disclosure generally relates to processes and systems for converting light alkanes to liquid hydrocarbon transportation fuels such as, benzene, toluene, and xylenes (BTX), gasoline and diesel.

BACKGROUND OF THE INVENTION

Light alkanes produced alongside tight oil and natural gas are typically of lesser value than olefins or liquid fuels. Increased production of these light alkanes from shale formations has created a market surplus of natural gas liquids (NGL). After being extracted in the field, a largely de-methanized NGL stream generally comprising C2-C7 hydrocarbons (also called Y-grade), is typically transported by pipelines from the production site to a fractionation facility where the NGL stream is separated into discrete components, including ethane, propane, iso-butane, n-butane, and natural gasoline (C5+).

Several commercial upgrading options exist for these various components. Some techniques utilize an initial steam-cracking step to upgrade these light alkanes, either individually or as a mixture. Other processes instead utilize catalytic processing in various forms. For example, the Oleflex™ process, the STAR™ process, the Catofin™ process, or the FBD™ process can be employed for propane and heavier alkanes, but generally include removal of ethane prior to upgrading of the heavier NGL components. This requirement is a disadvantage of these technologies, as is their high capital expense. As a result, commercial alternatives are not currently attractive.

Accordingly, a need exists for a more efficient process that allows efficient upgrading of a mixture of C2-C7 light alkanes (e.g., Y-grade or natural gas liquids) to liquid transportation fuels without first separating out one or more components.

BRIEF SUMMARY OF THE DISCLOSURE

The present disclosure generally relates to processes and systems for converting light alkanes to liquid hydrocarbon transportation fuels such as, benzene, toluene, and xylenes (BTX), gasoline and diesel. In one embodiment, a method for converting light hydrocarbon feedstock to produce liquid transportation fuels is provided. The method comprises contacting a light hydrocarbon feedstock comprising at least one C2-C7 alkane with a first fixed-bed catalyst in a first-stage conversion reactor to produce a first-stage effluent. In certain embodiments, the light hydrocarbon feedstock may comprise at least one C3-C5 alkane. The reaction conditions in the first-stage conversion reactor comprise a first temperature in a range from 400 degrees Celsius to 650 degrees Celsius and a first pressure in a range from 0 psig to 100 psig. The method further comprises separating the first-stage effluent in a first separator to produce a first condensed liquid hydrocarbon comprising at least five carbon atoms, and a gas phase product comprising at least one C2-C4 olefin. The method further comprises contacting the gas phase product with a second fixed-bed catalyst in a second-stage conversion reactor to produce a second-stage effluent. The reaction conditions in the second-stage conversion reactor comprise a second temperature less than the first temperature and in a range from 200 degrees Celsius to 400 degrees Celsius and a second pressure in a range from 0 psig to 500 psig. The method further comprises separating the second-stage effluent in a second separator to produce a second condensed liquid hydrocarbon comprising at least five carbon atoms and an unconverted stream comprising at least one C3-C4 alkane.

In certain embodiment, the light hydrocarbon feedstock comprises at least one C2-C7 alkane, for example, at least one C3-C5 alkane. In certain embodiments, the light hydrocarbon feedstock comprises at least one of propane, butane, or pentane. In certain embodiments, the light hydrocarbon feedstock comprises about 40 to 50 wt. % ethane, 25 to 30 wt. % propane, 15 to 20 wt. % butane, and 10 to 15 wt. % C5+. Optionally, the light hydrocarbon feedstock comprises at least 85 to 90 wt. % of hydrocarbon molecules that contain five or less carbon atoms, or four or less carbon atoms.

In certain embodiments, the first-stage conversion takes place at a first temperature that is greater than a second temperature of the second-stage conversion and the first-stage conversion takes place at a first pressure that is less than a second pressure of the second-stage conversion.

In certain embodiments, the first-stage conversion takes place at a temperature in a range from 450 degrees Celsius to 600 degrees Celsius and a pressure in a range of 0 psig to 90 psig. In certain embodiments, the first-stage conversion takes place at a temperature in a range from 450 degrees Celsius to 580 degrees Celsius and a pressure in a range of 0 psig to 80 psig. In certain embodiments, the first-stage conversion takes place at a temperature in a range from 450 degrees Celsius to 550 degrees Celsius and a pressure in a range of 0 psig to 70 psig.

In certain embodiments, the second-stage conversion takes place at a temperature in a range from 200 degrees Celsius to 400 degrees Celsius and a pressure in a range of 0 psig to 500 psig. In certain embodiments, the second-stage conversion takes place at a temperature in a range from 300 degrees Celsius to 400 degrees Celsius and a pressure in a range of 50 psig to 500 psig. In certain embodiments, the second-stage conversion takes place at a temperature in a range from 300 degrees Celsius to 350 degrees Celsius and a pressure in a range of 100 psig to 500 psig.

In certain embodiments, the temperature utilized for the second-stage conversion is at least 25 degrees Celsius less than the temperature utilized for the first-stage conversion. In certain embodiments, the pressure utilized for the second-stage conversion is equal to or greater than the pressure utilized for the first-stage conversion.

In certain embodiments, the first fixed-bed catalyst is suitable to activate the at least one C3-C5 alkane to produce the at least one C2-C4 olefin and the second fixed-bed catalyst is suitable to convert the at least one C2-C4 olefin to produce the second condensed liquid hydrocarbon comprising at least five carbon atoms.

In certain embodiments, the second fixed-bed catalyst is an aromatization catalyst. In certain embodiments, the second fixed-bed catalyst is an oligomerization catalyst.

In certain embodiments, the first fixed-bed catalyst and the second fixed-bed catalyst comprise at least one zeolite, optionally impregnated with at least one promotor metal such as, for example, zinc or gallium. In certain embodiments, the zeolite is a ZSM-5 zeolite. In certain embodiments, at least one of the first fixed-bed catalyst and the second fixed-bed catalyst comprise ZSM-5 zeolite, ZSM-11 zeolite, ZSM-22 zeolite, or a combination thereof.

In certain embodiments, the method further comprises adding a diluent to the first-stage conversion reactor. In certain embodiments, the diluent is a non-reactive diluent. In certain embodiments, the diluent includes any molecule that is less chemically reactive than the feedstock alkanes at the conditions of temperature and pressure maintained within the activation reactor. In certain embodiments, the diluent comprises methane, ethane, nitrogen, carbon dioxide, or a combination thereof.

In certain embodiments, the method further comprises conveying the unconverted stream comprising at least one C3-C4 alkane to the first-stage conversion reactor.

In certain embodiments, the method further comprises mixing the first condensed liquid hydrocarbon comprising at least five carbon atoms and the second condensed liquid hydrocarbon comprising at least five carbon atoms to produce a final liquid product hydrocarbons. The final liquid product hydrocarbons may be characterized by a boiling point that is within the boiling point range of diesel (193 degrees Celsius to 360 degrees Celsius) and/or BTX-rich gasoline (40 degrees Celsius to 193 degrees Celsius).

In another embodiment, a system for converting light hydrocarbon feedstock to produce liquid transportation fuels is provided. The system comprises a supply of light hydrocarbon feedstock comprising at least one C2-C7 alkane. In certain embodiments, the light hydrocarbon feedstock may comprise at least one C3-C5 alkane. The system further comprises a first-stage conversion reactor operable to receive the light hydrocarbon feedstock and facilitate contact between the light hydrocarbon feedstock and a first fixed-bed catalyst. The first-stage conversion reactor is further operable to maintain a first temperature in a range from 400 degrees Celsius to 650 degrees Celsius and a first pressure in a range from 0 psig to 100 psig. The system further comprises a first separator operable to receive and partially condense a first effluent from the first-stage conversion reactor, the first separator further comprising an outlet for a first condensed liquid comprising at least five carbon atoms and an outlet for a first gas phase product comprising at least one C2-C4 olefin. The system further comprises a second-stage conversion reactor operable to receive the first gas phase product from the first separator and facilitate contact between the first gas phase product and a second fixed-bed catalyst. The second-stage conversion reactor is further operable to maintain a second temperature in a range from 250 degrees Celsius to 400 degrees Celsius and a second pressure in a range from 0 psig to 500 psig. The system further comprises a second separator operable to receive and partially condense a second effluent from the second-stage conversion reactor, the second separator further comprising an outlet for a second condensed liquid comprising at least one five-carbon atoms and an outlet for an unconverted gas comprising at least one C3-C4 alkane.

In certain embodiments, the system further comprises a conduit operable to convey the unconverted gas of the second separator to the first-stage conversion reactor.

In certain embodiments, the system further comprises a diluent source fluidly coupled with the first-stage conversion reactor and operable to deliver a diluent to the first-stage conversion reactor.

In certain embodiments, the first fixed-bed catalyst is suitable to activate the least one C2-C7 alkane to produce the at least one C2-C4 olefin and the second fixed-bed catalyst is suitable to convert the at least one C2-C4 olefin to produce the second condensed liquid hydrocarbon comprising at least five carbon atoms.

In certain embodiments, the second fixed-bed catalyst is an aromatization catalyst. In certain embodiments, the second fixed-bed catalyst is an oligomerization catalyst.

In certain embodiments, the first fixed-bed catalyst and the second fixed-bed catalyst comprise at least one zeolite, optionally impregnated with at least one promotor metal such as, for example, zinc or gallium. In certain embodiments, the zeolite is a ZSM-5 zeolite. In certain embodiments, at least one of the first fixed-bed catalyst and the second fixed-bed catalyst comprise ZSM-5 zeolite, ZSM-11 zeolite, ZSM-22 zeolite, or a combination thereof.

The features, functions, and advantages that have been discussed can be achieved independently in various aspects or can be combined in yet other aspects, further details of which can be seen with reference to the following description and drawings.

BRIEF DESCRIPTION OF DRAWINGS

So that the manner in which the above-recited features of the present disclosure can be understood in detail, a more particular description of the disclosure briefly summarized above can be had by reference to aspects, some of which are illustrated in the appended drawings. It is to be noted, however, that the appended drawings illustrate only typical aspects of this disclosure and are therefore not to be considered limiting of its scope, for the disclosure can admit to other equally effective aspects.

FIG. 1 is a schematic illustration of a system for converting light hydrocarbon feedstock to produce liquid transportation fuels according to one or more implementations of the present disclosure.

To facilitate understanding, identical reference numerals have been used, wherever possible, to designate identical elements that are common to the figures. Additionally, elements of one aspect can be advantageously adapted for utilization in other aspects described herein.

DETAILED DESCRIPTION

The present disclosure provides processes to convert one or more light hydrocarbons to liquid transportation fuels. The process and systems are applicable to the conversion of a single light alkane or any mixture comprising predominantly light alkanes (e.g., C2-C7 alkanes, C3-C5 alkanes). One example of such a mixture is a naturally occurring mixture of hydrocarbons that is often referred to as "Y-grade" which is a raw natural gas liquid that predominantly comprises ethane, propane, butanes, and pentanes. The processes and systems disclosed herein include a two-stage zeolite conversion process that increases the overall yield of liquid products that can be utilized as transportation fuel, and in particular, increases the yield of larger hydrocarbon products that can be used as a diesel transportation fuel, or a component thereof.

Existing conventional light hydrocarbon aromatization methods utilize only a single-stage activation/aromatization reaction that occurs at a high temperature, for example, from about 475 degrees Celsius to about 600 degrees Celsius, and at a single pressure, for example, from about 1 to about 290 psig. In contrast, certain embodiments of the present disclosure convert a feedstock comprising at least one C2-C7 light alkane, for example, at least one C3-05 light alkane (predominantly C4-05) to a C5+ hydrocarbon product, for example, a BTX-rich hydrocarbon product, by decoupling the alkane activation (first-stage) from the oligomerization/aromatization (second-stage), which allows each conversion process to occur at optimal reaction conditions thus increasing the overall hydrocarbon product. The alkane activation or first-stage is operated at a higher temperature than the second-stage since light alkanes are much less reactive than light olefins. Since aromatization of olefins is more efficient at higher pressure, the second-stage is maintained at a higher pressure than the first-stage. Further, fixed-bed catalysts are used in each of the first-stage and the second-stage. Not to be bound by theory, but it is believed that utilizing fixed-bed catalysts facilitates maintaining a different pressure in each stage because the gaseous effluent remaining after partial condensation of the first-stage to remove, for example, C5+ pyrolysis gasoline, can be compressed and passed to the second-stage without requiring separation from the catalyst.

In its most basic form, the process comprises converting a feed comprising light hydrocarbons (e.g., C3-C5 alkanes) by contacting the feed with one or more zeolite catalysts in two separate stages with an intervening collection of C5+ hydrocarbon product between stages. A first-stage conversion reactor is optimized at a temperature (e.g., 400 to 650 degrees Celsius) and a pressure (e.g., 0 to 100 psig) to activate the light hydrocarbons to form a first-stage effluent. Between stages, the first-stage effluent is at least partially condensed separating liquid hydrocarbons comprising at least five hydrocarbon atoms from the first-stage effluent. The remaining unconverted gas-phase product of the first-stage effluent is then passed to a second-stage conversion reactor. In certain embodiments, the unconverted gas-phase product comprises at least one of hydrogen, methane, ethane, ethylene, propane, propylene, butane, butylene, and C5+. The second-stage conversion reactor is optimized to oligomerize and/or aromatize C2-C4 olefins of the unconverted gas-phase product at a lower temperature (e.g., 200 to 400 degrees Celsius) than the first-stage and an equal to or higher pressure (e.g., 0 to 500 psig) than the first-stage. The second-stage effluent is then at least partially condensed separating additional liquid hydrocarbons comprising at least five hydrocarbon atoms from an unconverted light hydrocarbon stream comprising four or less carbon atoms. The unconverted light hydrocarbon stream comprising four or less carbon atoms may be recycled to the first-stage conversion reactor for additional processing.

FIG. 1 is a schematic illustration of a system 100 for converting light hydrocarbon feedstock to produce liquid transportation fuels according to one or more implementations of the present disclosure. The system 100 includes a first-stage conversion reactor 120 and a second-stage conversion reactor 140. A mixture of light hydrocarbons is converted to liquid transportation fuel in the system 100. A light hydrocarbons stream 110 comprising at least one C2-C7 alkane, for example, at least one C3-C5 alkane such as, propane, butanes, and pentanes is used as feedstock. In certain embodiments, the light hydrocarbon feedstock comprises at least one of propane, butane, or pentane. In certain embodiments, the light hydrocarbon feedstock comprises about 40 to 50 wt. % ethane, 25 to 30 wt. % propane, 15 to 20 wt. % butane, and 10 to 15 wt. % C5+. Optionally, the light hydrocarbon feedstock comprises at least 85 to 90 wt. % of hydrocarbon molecules that contain five or less carbon atoms, or four or less carbon atoms. In certain embodiments, the light hydrocarbons stream 110 is fed directly into a first-stage conversion reactor 120. The first-stage conversion reactor 120 is operated at conditions for catalytically activating the C3-05 light alkanes and converting the light alkanes to hydrocarbons containing at least five carbon atoms.

The first-stage conversion reactor 120 includes a first fixed-bed catalyst 121 comprising at least one zeolite catalyst that converts the light hydrocarbons stream 110 into products that include olefins and hydrocarbons comprising at least five carbon atoms. In certain embodiments, the zeolite catalyst is an aluminosilicate zeolite catalyst. The aluminosilicate zeolite catalyst may further include metal promoters. Examples of metal promoters include metal promoters comprising gallium, zinc, or a combination of gallium and zinc. In certain embodiments, the first fixed-bed catalyst 121 is a zeolite catalyst selected from ZSM-5 zeolite, ZSM-11 zeolite, ZSM-22 zeolite, or a combination thereof. In certain embodiments, the first fixed-bed catalyst 121 is ZSM-5 zeolite. In the present disclosure, the term "conversion" is defined as any of the chemical reactions that occur during zeolite upgrading of hydrocarbons to liquid transportation fuels. Examples of such reactions include, but are not limited to: dehydrogenation, oligomerization, alkylation, hydrogenation, and/or cracking.

The first-stage conversion reactor 120 is maintained at reactions conditions of temperature and pressure that catalytically activate the light hydrocarbons stream 110 to produce a first-stage effluent (not depicted) comprising hydrocarbons that include C2-C4 olefins. In the first-stage conversion reactor 120, the reaction temperature is in a range from 400 degrees Celsius to 650 degrees Celsius, for example, in a range from 450 degrees Celsius to 600 degrees Celsius, such as in a range from 450 degrees Celsius to 580 degrees Celsius. In the first-stage conversion reactor 120, the reaction pressure is in a range from 0 psig to 100 psig, for example, in a range from 0 psig to 90 psig, such as, in a rang from 0 psig to 80 psig.

In certain embodiments, reaction conditions in the first-stage conversion reactor 120 comprise a first temperature in a range from 400 degrees Celsius to 650 degrees Celsius and a first pressure in a range from 0 psig to 100 psig. In certain embodiments, the first temperature is in a range from 450 degrees Celsius to 600 degrees Celsius and the first pressure is in a range from 0 psig to 90 psig. In certain embodiments, the first temperature is in a range from 450 degrees Celsius to 580 degrees Celsius and the first pressure is in a range from 0 psig to 80 psig. In certain embodiments, the first temperature is in a range from 450 degrees Celsius to 550 degrees Celsius and the first pressure is in a range from 0 psig to 70 psig.

In certain embodiments, the system 100 further includes a diluent source 170 fluidly coupled with the first-stage conversion reactor 120 and operable to deliver a diluent to the first-stage conversion reactor 120 via a conduit 171. Examples of the diluent include methane, ethane, nitrogen, carbon dioxide, or a combination thereof. Not to be bound by theory but it is believed that diluents may reduce the production of fuel gas during the first-stage conversion.

In certain embodiments, reaction of the light hydrocarbons stream 110 in the first-stage conversion reactor 120 is performed at a Weight Hourly Space Velocity (WHSV) of 0.1 to 10 $h^{-1}$, for example, at a WHSV of 1 to 2 $h^{-1}$, such as a WHSV of 1.5 to 2 $h^{-1}$.

The system 100 further includes a first product separator 130. The first-stage effluent exits the first-stage conversion reactor 120 and is conveyed via a first-stage effluent conduit 122 to the first product separator 130. The first product separator 130 is maintained at a temperature and pressure that allows the condensation of hydrocarbons comprising at least five carbon atoms (C5+), for example, pyrolysis gas. A first-stage condensed liquid hydrocarbons (not depicted) comprising the C5+ exits the first product separator 130 as a liquid by gravity flow via first separator conduit 132. The remaining gaseous effluent of the first-stage effluent comprises an unconverted light olefin stream (not depicted) comprising hydrocarbons characterized by four or less carbon atoms. The unconverted light olefin stream predominantly comprises unconverted C2-C4 olefins that were not converted to larger hydrocarbons in the first-stage conversion reactor 120. The remaining gaseous effluent either directly exits the first product separator 130 via an unconverted light olefin conduit 134 or is compressed to a higher pressure, remains in vapor-phase and exits the first product separator 130 via the unconverted light olefin conduit 134.

The unconverted light olefin stream is conveyed via the unconverted light olefin conduit 134 to the second-stage conversion reactor 140. The second-stage conversion reactor 140 includes a second fixed-bed catalyst 141 comprising at least one zeolite catalyst that converts the unconverted light olefin stream into larger hydrocarbon products that include hydrocarbons comprising at least five carbon atoms and optionally unreacted light alkanes, such as, C3-C4 alkanes. In certain embodiments, the zeolite catalyst is an aluminosilicate zeolite catalyst. The aluminosilicate zeolite catalyst may further include metal promoters. Examples of metal promoters include metal promoters comprising gallium, zinc, or a combination of gallium and zinc. In certain embodiments, the second fixed-bed catalyst 141 is selected from ZSM-5 zeolite, ZSM-11 zeolite, ZSM-22 zeolite, or a combination thereof. In certain embodiments, the second fixed-bed catalyst 141 is ZSM-5 zeolite.

In certain embodiments, where it is desirable to obtain a product that is rich in diesel-range liquid product, an oligomerization catalyst may be used while operating the second-stage conversion reactor at a reduced temperature and increased pressure. Speaking generally, the oligomerization catalyst may comprise any solid catalyst (or mixture of catalysts) characterized as possessing either Brønsted or Lewis acidic properties. In certain embodiments, the oligomerization catalyst is a zeolite or mixture of zeolites, or a reactive transition metal oxide. In certain embodiments, the oligomerization catalyst is ZSM-5, although many zeolites are well characterized as possessing oligomerization properties and may be suitable for use (either alone or in combination) with the processes and systems described herein. Other well-characterized oligomerization catalysts include, but are not limited to nickel oxides, aluminum alkyls, aluminum halides, perfluoroaryl boranes, oligomeric methyl aluminoxanes (including supported), perfluoroaryl boranes, fluoroarylanes, trityl borate, ammonium borate (and aluminate salts thereof), supported [PhNMe$_2$H$^+$][B(C$_6$F$_5$)$_4^-$] and borate anions and super acidic solid Brønsted acids, among others.

In certain embodiments, where it is desirable to obtain a product that is rich in BTX liquid product, an aromatization/alkylation catalyst may be used while operating the second-stage conversion reactor at an increased temperature. Speaking generally, the alkylation catalyst may comprise any catalyst characterized as either Brønsted or Lewis acidic. A wide variety of catalysts have been found to promote aromatic alkylation including, but not limited to, aluminum chloride, phosphoric acid, sulfuric acid, hydrofluoric acid, silica, alumina, sulfated zirconia, zeolites (including, for example, ZSM-5, ZSM-3, ZSM-4, ZSM-18, ZSM-20, zeolite-beta, H-Y, MCM-22, MCM-36 and MCM-49). In certain embodiments, the alkylation catalyst simultaneously promotes alkylation of aromatics and oligomerization of olefins present in the mixed effluent.

In certain embodiments, the second fixed-bed catalyst 141 of the second-stage conversion reactor 140 is the same as the first fixed-bed catalyst 121 of the first-stage conversion reactor 120. In certain embodiments, the second fixed-bed catalyst 141 of the second-stage conversion reactor 140 is different from the first fixed-bed catalyst 121 of the first-stage conversion reactor 120.

The second-stage conversion reactor 140 is maintained at reaction conditions of temperature and pressure that oligomerize/aromatize the unconverted light olefin stream produced in the first-stage conversion reactor 120 to produce a second-stage effluent (not depicted). In certain embodiments, conditions of temperature and pressure are maintained in the second-stage conversion reactor 140 to favor the oligomerization/aromatization of C2-C4 olefins to form larger hydrocarbon products that comprise at least five carbon atoms, for example, at least 7 carbons, such as hydrocarbon products characterized by a boiling point that is within the boiling point range of diesel (193 degrees Celsius to 360 degrees Celsius) and/or BTX-rich gasoline (40 degrees Celsius to 193 degrees Celsius).

In the second-stage conversion reactor 140, the reaction temperature is in a range from 200 degrees Celsius to 400 degrees Celsius, for example, in a range from 250 degrees Celsius to 400 degrees Celsius, such as in a range from 300 degrees Celsius to 400 degrees Celsius. In the second-stage conversion reactor 140, the reaction pressure is in a range from 0 psig to 500 psig, for example, in a range from 50 psig to 500 psig, such as, in a range from 100 psig to 500 psig.

In certain embodiments, reaction conditions in the second-stage conversion reactor 140 comprise a second temperature in a range from 200 degrees Celsius to 400 degrees Celsius and a second pressure in a range from 0 psig to 500 psig. In certain embodiments, the second temperature is in a range from 250 degrees Celsius to 400 degrees Celsius and the second pressure is in a range from 50 psig to 500 psig. In certain embodiments, the second temperature is in a range from 300 degrees Celsius to 400 degrees Celsius and the second pressure is in a range from 100 psig to 500 psig. In certain embodiments, the second temperature is in a range from 300 degrees Celsius to 350 degrees Celsius and the second pressure is in a range from 100 psig to 450 psig.

In certain embodiments, the first-stage conversion takes place at a first temperature in a range from 400 degrees Celsius to 650 degrees Celsius, for example, in a range from 480 degrees Celsius to 580 degrees Celsius, and at a first pressure in a range from 0 psig to 100 psig, while the subsequent second-stage conversion typically takes place at a second temperature in a range from 200 degrees Celsius to 400 degrees Celsius and a second pressure in a range from about 300 psig to 500 psig. In certain embodiments, the first-stage conversion takes place at a first temperature in a range from 500 degrees Celsius to 600 degrees Celsius and a first pressure in a range from 0 psig to 100 psig, while the subsequent second-stage conversion takes place at a second temperature in a range from 320 degrees Celsius to 365 degrees Celsius and a pressure in a range from 100 psig to 500 psig.

In certain embodiments, the temperature utilized for the second-stage conversion is at least 25 degrees Celsius lower (optionally at least 40 degrees Celsius lower, optionally at least 50 degrees Celsius lower, optionally at least 60 degrees Celsius lower) than the temperature utilized for the first-stage conversion. In certain embodiments, the pressure utilized for the second-stage conversion is equal to or at least 100 psig higher (optionally at least 300 psig higher) than the pressure utilized for the first-stage conversion.

In certain embodiments, reaction of the unconverted light olefin stream in the second-stage conversion reactor 140 is performed at a Weight Hourly Space Velocity (WHSV) of 0.1 to 10 $h^{-1}$, for example, at a WHSV of 1 to 2 $h^{-1}$, such as a WHSV of 1.5 to 2 $h^{-1}$.

The system 100 further includes a second product separator 150. The second-stage effluent from the second-stage conversion reactor 140 is conveyed via a second-stage outlet conduit 142 to the second product separator 150 that separates the second-stage effluent into two fractions. A second condensed liquid hydrocarbons comprising hydrocarbon molecules containing at least five carbon atoms exits the bottom of the second product separator 150 via a second separator C5+ product conduit 152. In certain embodiments, the second-stage condensed liquid hydrocarbons are combined with the first-stage condensed liquid hydrocarbons from the first product separator 130 to produce a final liquid hydrocarbon product. The final liquid hydrocarbon product 154 is characterized by a boiling point that is within the boiling point range of diesel (193 degrees Celsius to 360 degrees Celsius) and/or BTX-rich gasoline (40 degrees Celsius to 193 degrees Celsius).

In certain embodiments, the final liquid hydrocarbon product 154 may be blended into conventional liquid transportation fuels or additionally processed (i.e., hydrotreating) prior to use as a transportation fuel. In certain embodiments, hydrocarbons in the diesel boiling point range may be separated from the final liquid hydrocarbon product, then further hydrotreated to reduce olefin and aromatic contents via hydrotreating or hydrogenation using a conventional hydrotreating catalyst (such as NiMo, CoMo, etc.) or a precious metal catalyst (such as $Pt/Al_2O_3$, $Pd/Al_2O_3$, or Pd/C, etc.).

Any remaining unconverted light gases (not depicted) leave the second product separator 150 via unconverted gas conduit 156, which is recycled to the first-stage conversion reactor 120 to be processed in the first-stage conversion reactor 120. A purge stream 158 comprising methane, ethane, nitrogen, carbon dioxide, or a combination thereof leaves the second product separator 150 via a purge conduit 160 to prevent an accumulation of inert components in the system 100 that may excessively dilute the light hydrocarbon feedstock in the first-stage conversion reactor 120.

EXAMPLES

The following non-limiting examples are provided to further illustrate aspects described herein. However, the examples are not intended to be all-inclusive and are not intended to limit the scope of the aspects described herein. The particular materials and amounts thereof, as well as other conditions and details recited in these examples should not be used to limit the implementations described herein. Examples of the present disclosure are identified by the letter "E" followed by the sample number while comparative examples, which are not examples of the present disclosure are designated by the letter "X" followed by the sample number.

Example 1 (E1)

To demonstrate the effectiveness of the dual-stage conversion process disclosed herein, a conventional single-stage zeolite conversion of light alkanes was compared to one embodiment of the inventive dual-stage process disclosed herein. A light alkane feedstock that comprised 100 wt. % n-butane was used. For comparative example X1, the light alkane feedstock was introduced into a single-stage conversion reactor containing ZSM-5 zeolite catalyst (catalyst A). The single-stage conversion reactor was maintained at a temperature of 531 degrees Celsius, a pressure of 0 psig, and a WHSV of 0.5 $hr^{-1}$. The effluent from this single-stage conversion reactor was then condensed to recover C5+ liquid hydrocarbons. The results for comparative example X1 are depicted in Table I.

For comparative example X2, the light alkane feedstock was introduced into a single-stage conversion reactor containing catalyst A. The single-stage conversion reactor was maintained at a temperature of 580 degrees Celsius, a pressure of 0 psig, and a WHSV of 1.5 $hr^{-1}$. The effluent from this single-stage conversion reactor was then condensed to recover C5+ liquid hydrocarbons. The results for comparative example X2 are also depicted in Table I.

For Example E1, the light alkane feedstock was introduced into a first-stage conversion reactor containing catalyst A. The first-stage conversion reactor was maintained at a temperature of 580 degrees Celsius, a pressure of 0 psig, and a WHSV of 1.5 $hr^{-1}$. The effluent from this first-stage conversion reactor was then condensed to recover C5+ liquid hydrocarbons.

Hydrocarbons that remained unconverted by the conditions of the first-stage reactor were next introduced to a second-stage conversion reactor containing catalyst A and maintained at 340 degrees Celsius and a pressure of 0 psig to convert remaining light olefins. Analysis of the combined liquid products condensed from the reactor was combined with the liquid product from the first conversion/upgrading reactor and the overall product distribution is reported in Table I. The dual-stage conversion process was observed to clearly improve the overall liquid yield as well as the yield of product hydrocarbons having a boiling point in the range of BTX. The selectivity of C5+ condensable hydrocarbons collected after the first-stage and second-stage was 49.9 wt. % (includes gasoline-range, diesel-range, and BTX-range hydrocarbons). As depicted in Table I, the selectivity of C5+ liquid recovered in E1 (49.9 wt. %) was significantly greater than the selectivity of C5+ liquid recovered in either X1 (27.9 wt. %) or X2 (30.2 wt. %), while all three cases showed similar levels of n-butane conversion.

TABLE I

Comparison of single-stage operation versus dual-stage operation using Catalyst A.

| Example No. | X1 | X2 | E1 |
| --- | --- | --- | --- |
| Operation | Single-stage | Single-stage | Dual-stage |
| Temp (° C.) | 531 | 580 | 580/340 |
| WHSV ($hr^{-1}$) | 0.5 | 1.5 | 1.5 |
| Catalyst(s) | Catalyst A | Catalyst A | Catalyst A/ Catalyst A |

TABLE I-continued

Comparison of single-stage operation versus dual-stage operation using Catalyst A.

| Example No. | X1 | X2 | E1 |
|---|---|---|---|
| Product Selectivity (wt. %) | | | |
| H2 and C1-C2 | 26.7 | 27.8 | 28.8 |
| C3-C4 paraffins | 31.2 | 13.5 | 16.2 |
| C2-C4 olefins | 14.2 | 28.5 | 5.2 |
| C5+ liquid | 27.9 | 30.2 | 49.9 |
| n-C4 conversion (%) | 70 | 68 | 71 |

Example 2 (E2)

For comparative example X3, the light alkane feedstock was introduced into a single-stage conversion reactor containing a zeolite-based catalyst (catalyst B). The single-stage conversion reactor was maintained at a temperature of 480 degrees Celsius, a pressure of 0 psig, and a WHSV of 0.5 $hr^{-1}$. The effluent from this single-stage conversion reactor was then condensed to recover C5+ liquid hydrocarbons. The results for comparative example X3 are depicted in Table II.

For comparative example X4, the light alkane feedstock was introduced into a single-stage conversion reactor containing catalyst B. The single-stage conversion reactor was maintained at a temperature of 520 degrees Celsius, a pressure of 0 psig, and a WHSV of 1.5 $hr^{-1}$. The effluent from this single-stage conversion reactor was then condensed to recover C5+ liquid hydrocarbons. The results for comparative example X4 are also depicted in Table II.

For Example E2, the light alkane feedstock was introduced into a first-stage conversion reactor containing catalyst B. The first-stage conversion reactor was maintained at a temperature of 520 degrees Celsius, a pressure of 0 psig, and a WHSV of 1.5 $hr^{-1}$. The effluent from this first-stage conversion reactor was then condensed to recover C5+ liquid hydrocarbons.

Hydrocarbons that remained unconverted by the conditions of the first-stage reactor were next introduced to a second-stage conversion reactor containing catalyst B and maintained at 340 degrees Celsius and a pressure of 0 psig to convert remaining light olefins. Analysis of the combined liquid products condensed from the reactor was combined with the liquid product from the first conversion/upgrading reactor and the overall product distribution is reported in Table II. The dual-stage conversion process was observed to clearly improve the overall liquid yield as well as the yield of product hydrocarbons having a boiling point in the range of BTX. The selectivity of C5+ condensable hydrocarbons collected after the first-stage and second-stage was 59.6 wt. % (includes gasoline-range, diesel-range, and BTX-range hydrocarbons). As depicted in Table II, the quantity of C5+ liquid recovered in E2 (59.6 wt. %) was significantly greater than the quantity of C5+ liquid recovered in either X3 (51.0 wt. %) or X4 (48.6 wt. %).

TABLE II

Comparison of single-stage operation versus dual-stage operation using Catalyst B.

| Example No. | X3 | X4 | E2 |
|---|---|---|---|
| Operation | Single-stage | Single-stage | Dual-stage |
| Temp (° C.) | 480 | 520 | 520/340 |
| WHSV (hr-1) | 0.5 | 1.5 | 1.5 |
| Catalyst(s) | Catalyst B | Catalyst B | Catalyst B/ Catalyst B |
| Product Selectivity (wt. %) | | | |
| H2 and C1-C2 | 29.1 | 26.0 | 26.4 |
| C3-C4 paraffins | 16.4 | 13.6 | 11.1 |
| C2-C4 olefins | 3.5 | 11.7 | 2.8 |
| C5+ liquid | 51.0 | 48.6 | 59.6 |
| n-C4 conversion (%) | 82 | 72 | 74 |

As demonstrated herein, the dual-stage conversion process described herein provides higher C5+ liquid yield than conventional single-stage processes, which is beneficial to the process economics due to higher selectivity of the dual-stage conversion process relative to conventional single-stage conversion processes.

The descriptions of the various aspects of the present disclosure have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein. While the foregoing is directed to aspects of the present disclosure, other and further aspects of the present disclosure can be devised without departing from the basic scope thereof.

What is claimed is:

1. A method for converting light hydrocarbon feedstock to produce liquid transportation fuels, the method comprising:
    contacting a light hydrocarbon feedstock comprising at least one $C_3$-$C_5$ alkane with a first fixed-bed catalyst in a first-stage conversion reactor to produce a first-stage effluent, wherein reaction conditions in the first-stage conversion reactor comprise a first temperature in a range from 400 degrees Celsius to 650 degrees Celsius and a first pressure in a range from 0 psig to 100 psig;
    separating the first-stage effluent in a first separator to produce a first condensed liquid hydrocarbon comprising at least five carbon atoms, and a gas phase product comprising at least one $C_2$-$C_4$ olefin;
    contacting the gas phase product with a second fixed-bed catalyst in a second-stage conversion reactor to produce a second-stage effluent, wherein reaction conditions in the second-stage conversion reactor comprise a second temperature lower than the first temperature and in a range from 200 degrees Celsius to 400 degrees Celsius and a second pressure in a range from 0 psig to 500 psig; and
    separating the second-stage effluent in a second separator to produce a second condensed liquid hydrocarbon comprising at least five carbon atoms and an unconverted stream comprising at least one $C_3$-$C_4$ alkane.

2. The method of claim 1, wherein the first temperature is in a range from 480 degrees Celsius to 580 degrees Celsius.

3. The method of claim 1, wherein the first temperature is in a range from 450 degrees Celsius to 550 degrees Celsius.

4. The method of claim 1, wherein the first pressure is in a range from 0 psig to 80 psig.

5. The method of claim 1, wherein the second temperature is in a range from 250 degrees Celsius to 400 degrees Celsius.

6. The method of claim 1, wherein the second temperature is in a range from 250 degrees Celsius to 350 degrees Celsius.

7. The method of claim 1, wherein the second pressure is in a range from 100 psig to 500 psig.

8. The method of claim 1, wherein the second fixed-bed catalyst is an aromatization catalyst.

9. The method of claim 1, wherein the second fixed-bed catalyst is an oligomerization catalyst.

10. The method of claim 1, wherein the first fixed-bed catalyst and the second fixed-bed catalyst comprise at least one zeolite.

11. The method of claim 1, wherein the first fixed-bed catalyst and the second fixed-bed catalyst comprise ZSM-5 zeolite, ZSM-11 zeolite, ZSM-22 zeolite, or a combination thereof.

12. The method of claim 1, wherein the gas phase product comprises hydrogen, methane, ethane, ethylene, propane, propylene, butane, butylene, and $C_{5+}$.

13. The method of claim 1, further comprising adding a diluent to the first-stage conversion reactor.

14. The method of claim 13, wherein the diluent is selected from methane, ethane, nitrogen, carbon dioxide, or a combination thereof.

15. The method of claim 1, further comprising conveying the unconverted stream comprising at least one $C_3$-$C_4$ alkane to the first-stage conversion reactor.

16. A system for converting light hydrocarbon feedstock to produce liquid transportation fuels, the system comprising:
 a supply of light hydrocarbon feedstock comprising at least one $C_3$-$C_5$ alkane;
 a first-stage conversion reactor operable to receive the light hydrocarbon feedstock and facilitate contact between the light hydrocarbon feedstock and a first fixed-bed catalyst, the first-stage conversion reactor further operable to maintain a first temperature in a range from 400 degrees Celsius to 650 degrees Celsius and a first pressure in a range from 0 psig to 100 psig;
 a first separator operable to receive and partially condense a first effluent from the first-stage conversion reactor, the first separator further comprising an outlet for a first condensed hydrocarbon liquid comprising at least five carbon atoms and an outlet for a first gas phase product comprising at least one $C_2$-$C_4$ olefin;
 a second-stage conversion reactor operable to receive the first gas phase product from the first separator and facilitate contact between the first gas phase product and a second fixed-bed catalyst, the second-stage conversion reactor further operable to maintain a second temperature in a range from 200 degrees Celsius to 400 degrees Celsius and a second pressure in a range from 0 psig to 500 psig; and
 a second separator operable to receive and partially condense a second effluent from the second-stage conversion reactor, the second separator further comprising an outlet for a second condensed liquid hydrocarbon comprising at least one five carbon atoms and an outlet for an unconverted gas comprising at least one $C_3$-$C_4$ alkane.

17. The system of claim 16, further comprising a conduit operable to convey the unconverted gas of the second separator to the first-stage conversion reactor.

18. The system of claim 16, wherein the first fixed-bed catalyst and the second fixed-bed catalyst comprise at least one zeolite.

19. The system of claim 16, wherein the first fixed-bed catalyst and the second fixed-bed catalyst comprise ZSM-5 zeolite, ZSM-11 zeolite, ZSM-22 zeolite, or a combination thereof.

20. The system of claim 16, further comprising a non-reactive diluent source fluidly coupled with the first-stage conversion reactor and operable to deliver a non-reactive diluent to the first-stage conversion reactor.

* * * * *